United States Patent [19]

Nappa

[11] Patent Number: 4,847,427

[45] Date of Patent: Jul. 11, 1989

[54] PROCESS FOR PREPARING FLUOROCARBON POLYETHERS

[75] Inventor: Mario J. Nappa, Newark, Del.

[73] Assignee: E. I. Du Pont de Nemours and Company, Wilmington, Del.

[21] Appl. No.: 181,044

[22] Filed: Apr. 13, 1988

[51] Int. Cl.$^4$ ........................ D07C 41/02; C07C 41/22
[52] U.S. Cl. .................................... 568/615; 568/601; 568/603; 568/604; 568/677
[58] Field of Search ............... 568/615, 601, 603, 604, 568/677

[56] References Cited

U.S. PATENT DOCUMENTS 3,242,218 3/1966 Miller .................................. 260/615
3,399,179 8/1968 Grakaukas ......................... 260/92.1

FOREIGN PATENT DOCUMENTS 8602390 5/1987 World Int. Prop. O. .

Primary Examiner—Howard T. Mars
Attorney, Agent, or Firm—Charles E. Krukiel

[57] ABSTRACT

An improvement in a process for neutralizing perfluorinated carboxylic acids to make fluorocarbon polyethers in which the acid is heated with fluorine in the presence of a metal fluoride.

5 Claims, No Drawings

PROCESS FOR PREPARING FLUOROCARBON POLYETHERS

BACKGROUND OF THE INVENTION

The present invention relates to polyethers which are derived from the polymerization of a perfluoroolefin epoxide, and, more particularly, to an improved process for neutralizing acid end groups of such polyethers by replacing them with fluorine radicals.

U.S. Pat. No. 3,242,218 describes a process for preparing fluorocarbon polyethers of the following structure:

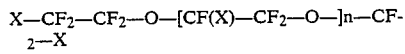

where n is a positive integer including zero and represents the number of $-CF(X)-CF_2-O-$ units in the molecule and where X is a member of the class consisting of fluorine and the perfluoromethyl radical. The process involves the polymerization of a perfluoroolefin epoxide, such as hexafluoropropylene epoxide and tetrafluoroethylene epoxide, to form a perfluorinated acid having the general formula

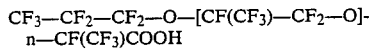

where n can range from 0 to 35 inclusive, and then heating the acid with fluorine to replace the carboxylic end group with a fluorine radical. The decarboxylation is generally very slow, and, although raising the reaction temperature can raise the reaction rate, elevating temperatures may result in vapor phase explosions.

U.S. Pat. No. 3,399,179 describes the decarboxylation of organic carboxylic acids with fluorine. It is stated that one or more carboxy groups can be replaced directly by fluorine atoms without regard for the exact nature of the organic portion of the molecule since the fluorination reaction occurs at the site of the carboxy group. However, the use of a substantially inert moderator, i.e., a polar or non-polar material in which the acid compound being decarboxylated is at least partially soluble, is an essential part of the decarboxylation reaction.

SUMMARY OF THE INVENTION

The present invention is an improvement in a process for making perfluoropolyethers in which the perfluoropolyethers have been derived from a process comprising:

(a) polymerizing a perfluoroolefin epoxide to form an acid fluoride;
(b) hydrolyzing the acid fluoride to form a perfluoropolyether carboxylic acid; and
(c) neutralizing the acid by heating with fluorine to replace the carboxylic acid end group with a fluorine radical.

The improvement comprises heating the perfluoropolyether carboxylic acid to a temperature in the range of about 50° C. to 300° C., preferably 100° C. to 135° C., in the presence of a metal fluoride salt selected from sodium fluoride and potassium fluoride. The metal fluoride salt acts as a base to remove a proton from the perfluoropolyether carboxylic acid intermediate to generate a perfluoropolyether carboxylate anion which reacts rapidly with fluorine.

It has also been discovered that, unlike the addition of hydroxides of metal cations to organic carboxylic acids followed by fluorination, the addition of metal fluorides to perfluorocarboxylic acids according to the present invention unexpectedly reduces the corrosion of reaction vessels made of monel.

DETAILED DESCRIPTION OF THE INVENTION

Perfluoropolyethers to which the improvement of this invention is applicable may have the following structure:

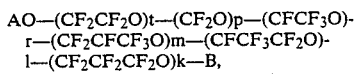

where A may be $CF_3$, $CF_2CF_3$, $CF_2CF_2CF_3$, or $CF(CF_3)_2$; B may be $CF_2COF$, $CF_2OCOF$, $CF_2CF_2OCOF$, $CFCF_3COF$, $CF_2CFCF_3OCOF$, $CF_2CF_2CF_2COF$, or $CFCF_3CF_2OCOF$; and t, p, r, m, l, and k are positive integers including zero. In the following discussion the perfluorinated organic portion of the perfluoropolyether molecule will be designated Rf for ease of understanding this invention, i.e., this invention is not limited by the perfluorinated organic portion of the molecule.

The preparation of perfluoropolyethers to which this invention is applicable is described in U.S. Pat. No. 3,214,478 and in U.S. Pat. No. 3,242,218, the teachings of which are incorporated herein by reference. The preparation involves polymerizing a perfluoroolefin epoxide, such as, for example, hexafluoropropylene epoxide and tetrafluoroethylene epoxide, to form an acid fluoride, and then hydrolyzing the acid fluoride to form the corresponding perfluoroether carboxylic acid, RfCOOH. The perfluoroether carboxylic acid is then neutralized by replacing the acid end group with a fluorine radical, for example, by reaction with elemental fluorine at a temperature in the range of about 50° to 300° C. The reaction rate is generally very low. It can be raised by increasing the temperature, however, elevated temperatures can result in a loss of low molecular weight components due to entrainment by fluorine or an inert diluent, such as nitrogen, which is normally bubbled through the perfluoroether carboxylic acid liquid during the reaction. In addition, elevated temperatures can also result in vapor phase explosions due to an increase in the amount of organic material in the vapor phase during the reaction.

U.S. Pat. No. 3,399,179 describes an alternative method whereby a —COOH group in an organic carboxylic acid or mixture of such acids may be directly replaced by a fluorine atom. The reaction between fluorine and the organic compound is carried out in the presence of a substantially inert normally liquid moderator, such as, for example, a polar or non-polar material in which the acid compound being decarboxylated is at least partially soluble. Use of the moderator is described as an essential part of the decarboxylation reaction.

According to the present invention a perfluorinated carboxylic acid can be neutralized, i.e., the —COOH group can be directly replaced with a fluorine radical, without the need for an inert liquid moderator and at temperatures substantially lower than known in the art by adding a metal fluoride salt directly to the acid liquid prior to the reaction. It has unexpectedly been found that the metal fluoride salt acts as a base to remove a proton from the perfluoroether carboxylic acid to generate a perfluoroether carboxylate anion. It is only in the absence of a liquid moderator that a metal fluoride (MF) is basic enough to remove a proton from a perfluoroether carboxylic acid and form the corresponding anion which reacts rapidly with fluorine according to the following equations:

$$RfCOOH + MF \rightarrow RfCOOM + HF \quad (1)$$

$$RfCOOM + F_2 \rightarrow RfCOOF + MF \quad (2)$$

$$RfCOOF \rightarrow RfF + CO_2 \quad (3)$$

In carrying out the process improvement of this invention, less than a stoichiometric amount of metal fluoride is needed to give higher purity perfluoropolyethers. Since a metal fluoride (MF) is generated in step 2 as shown above, it can be reused in step 1 to make more perfluoroether carboxylate anion (RfCOOM) and thereby improve process economics.

The neutralized products obtained according to the improvement of this invention show the same types, but lower amounts, of neutral end groups which are obtained by the conventional fluorination processes at higher temperature. Temperatures can range from 50° to 300° C., but preferably the neutralization reaction is carried out at a temperature in the range of about 150° to 250° C., and more preferably between 100° and 135° C. Shown below in Table 1 are the results of four laboratory runs in which the quantity of metal fluoride added to the perfluoroether carboxylic acid liquid prior to neutralization with fluorine was varied. All reactions were run between 100° to 135° C.

TABLE 1

| Run # | HEC | AF | Acid | Comments |
|---|---|---|---|---|
| 1 | 16 | 11 | 2 | No metal fluoride present |
| 2 | 0 | 10 | 3 | 0.5 molar equiv. of NaF |
| 3 | 0 | 7 | 2 | 1.0 molar equiv. of NaF |
| 4 | 0 | 3 | 2 | 2.4 molar equiv. of KF |

HEC = micromoles of hydro end cap per gram of perfluoropolyether.
AF = micromoles of acid fluoride per gram of perfluoropolyether.
ACID = micromoles of unreacted acid per gram of perfluoropolyether.

It is known, moreover, that hydroxides of metal salts in the presence of substantially inert liquid moderators as previously described can lead to highly explosive and highly corrosive oxygen difluoride. Quite unexpectedly, the addition of metal fluorides to perfluoropolyether carboxylic acids according to this invention reduces the corrosion of the monel reaction vessels in which this reaction is normally carried out. Shown below in Table 2 are the corrosion rates which were recorded during the process of neutralizing perfluoroether carboxylic acids with molecular fluorine. In run 2, the addition of only 0.5 molar equivalents of NaF reduced the rate of corrosion. CsF is known to enhance corrosion of monel, which is a preferred material of construction for fluorine reaction vessels. NaF unexpectedly retards this corrosive tendency.

TABLE 2

| Run # | Corrosion (cm/month) | Comments |
|---|---|---|
| 1 | .00389 | No metal fluoride present |
| 2 | .00325 | 0.5 molar equiv. of NaF |
| 3 | .03777 | 0.5 molar equiv. of CsF |
| 4 | .00955 | 0.5 molar equiv. of NaF and 0.5 molar equiv. of CsF |

Along with increasing the quality of the product obtained from the neutralization process and reducing reaction vessel corrosion, the improvement of this invention makes it possible to achieve exhaustive neutralization of the corresponding acid at temperatures much lower than those described in the art, for example, lower than those described in U.S. Pat. No. 3,242,218.

This invention also permits the economical neutralization of lower molecular weight perfluoropolyether carboxylic acids (MW 500-1000), a range that was too low for the prior art processes described hereinabove. Moreover, the lower operating temperatures of this invention afford product perfluoropolyethers which are devoid of any hydro end cap, an unwanted by-product formed by thermal decarboxylation of perfluoropolyether carboxylic acid.

The improved process of this invention makes it possible to increase the velocity of fluorine addition to the reaction by as little as 44% with no discernable penalty. One would normally expect a reduction in fluorine efficiency. In practice, less fluorine is required for the neutralization which makes the process more economical to operate.

The improved process of this invention is illustrated in more detail in the following examples. The amount of residual acid functional groups, acid fluoride functional groups, and hydrogen (as hydro end capped product) was determined by infrared spectroscopy. The infrared spectra were measured on a Nicolet 7199 Fourier transform infrared spectrophotometer and analyzed for CH, COF, and COOH.

EXAMPLE 1

Perfluoropolyether having terminal carboxylic acid groups was prepared according to the process disclosed by U.S. Pat. No. 3,242,218. The product required no purification and was used as received from the hydrolyzer, which converted the acid fluoride product of hexafluoropropene oxide polymerization to a perfluoropolyether carboxylic acid. Perfluoropolyether (350 gm, 0.117 mole) having terminal carboxylic acid groups and of average molecular weight 3000 gm/mole and potassium fluoride (16.0 gm, 0.275 mole) were heated to 100° C. in an all monel fluorinator, while purging with nitrogen (100 sccm) for 35 minutes. Molecular fluorine diluted with nitrogen was added as follows: 4.8% for 10 minutes, 11.1% for 10 minutes, 20.0% for 10 minutes, 33.3% for 10 minutes and 50.0% for 132 minutes (all with a nitrogen flow rate of 40 sccm). The contents of the reactor were cooled to 120° C. and urged with nitrogen (100 sccm) for 60 minutes. Analysis of the untreated product showed 3 micromoles of acid fluoride/gram of perfluoropolyether, 2 micromoles of acid/gram of perfluoropolyether, and no hydro encapped product.

EXAMPLE 2

Perfluoropolyether having terminal carboxylic acid groups was prepared according to the process disclosed by U.S. Pat. No. 3,242,218. The product required no purification and was used as received from the hydrolyzer, which converted the acid fluoride product of hexafluoropropene oxide polymerization to a perfluoropolyether carboxylic acid. Perfluoropolyether (350 gm, 0.117 mole) having terminal carboxylic acid groups and of average molecular weight 3000 gm/mole and sodium fluoride (4.90 gm., 117 mole) were heated to 100° C. in an all monel fluorinator, while purging with nitrogen (100 sccm) for 30 minutes. Molecular fluorine diluted with nitrogen was added as follows: 4.8% for 10 minutes, 11.1% for 10 minutes, 20.0% for 10 minutes, 33.3% for 10 minutes and 50.0% for 132 minutes (all with a nitrogen flow rate of 40 sccm). The contents of the reactor were cooled to 120° C. and purged with nitrogen (100 sccm) for 60 minutes. Analysis of the untreated product showed 7 micromoles of acid fluoride/gram of perfluoropolyether, 2 micromoles of acid/gram of perfluoropolyether, and no hydro endcapped product.

EXAMPLE 3

Perfluoropolyether having terminal carboxylic acid groups was prepared according to the process disclosed by U.S. Pat. No. 3,242,218. The product required no purification and was used as received from the hydrolyzer, which converted the acid fluoride product of hexafluoropropene oxide polymerization to a perfluoropolyether carboxylic acid. Perfluoropolyether (350 gm, 0.117 mole) having terminal carboxylic acid groups and of average molecular weight 3000 gm/mole and sodium fluoride (2.45 gm, 0.058 mole) were heated to 100° C. in an all monel fluorinator, while purging with nitrogen (100 sccm) for 30 minutes. Molecular fluorine diluted with nitrogen was added as follows: 4.8% for 10 minutes, 11.1% for 10 minutes, 20.0% for 10 minutes, 33.3% for 10 minutes and 50.0% for 132 minutes (all with a nitrogen flow rate of 40 sccm). The contents of the reactor were cooled to 120° C. and purged with nitrogen (100 accm) for 60 minutes. Analysis of the untreated product showed 10 micromoles of acid fluoride/gram of perfluoropolyether, 3 micromoles of acid/gram of perfluoropolyether, and no hydro encapped product.

EXAMPLE 4

Perfluoropolyether having terminal carboxylic acid groups was prepared according to the process disclosed by U.S. Pat. No. 3,242,218. The product required no purification and was used as received from the hdyrolyzer, which converted the acid fluoride product of hexafluoropropene oxide polymerization to a perfluoropolyether carboxylic acid. Perfluoropolyether (350 gm, 0.117 mole) having terminal carboxylic acid groups and of average molecular weight 3000 gm/mole and sodium fluoride (2.45 gm, 0.058 mole) and a monel corrosion coupon were heated to 100° C. in an all monel fluorinator, while purging with nitrogen (100 sccm) for 29 minutes. Molecular fluorine diluted with nitrogen was added as follows: 4.8% for 10 minutes, 11.1% for 10 minutes, 20.0% for 10 minutes, 33.3% for 10 minutes and 50.0% for 132 minutes (all with a nitrogen flow rate of 40 sccm). The contents of the reactor were cooled to 120° C. and urged with nitrogen (100 sccm) for 60 minutes. Analysis of the monel corrosion coupon showed corrosion at a rate of 0.00325 cm/month.

EXAMPLE 5

Perfluoropolyether having terminal carboxylic acid groups was prepared according to the process disclosed by U.S. Pat. No. 3,242,218. The product required no purification and was used as received from the hydrolyzer, which converted the acid fluoride product of hexafluoropropene oxide polymerization to a perfluoropolyether carboxylic acid. Perfluoropolyether (350 gm, 0.117 mole) having terminal carboxylic acid groups and of average molecular weight 3000 gm/mole was heated to 100° C. in an all monel fluorinator, while purging with nitrogen (100 sccm) for 35 minutes. Molecular fluorine diluted with nitrogen was added as follows: 4.8% for 10 minutes, 11.1% for ten minutes, 20.0% for 10 minutes, 33.3% for 10 minutes and 50.0% for 132 minutes (all with a nitrogen flow rate of 40 sccm). The contents of the reactor were cooled to 120° C. and purged with nitrogen (100 sccm) for 60 minutes. Analysis of the untreated product showed 11 micromoles of acid fluoride/gram of perfluoropolyether, 2 micromoles of acid/gram of perfluoropolyether and 16 micromoles of HEC (hydro encapped product).

EXAMPLE 6

Perfluoropolyether having terminal carboxylic acid groups was prepared according to the process disclosed by U.S. Pat. No. 3,242,218. The product required no purification and was used as received from the hydrolyzer, which converted the acid fluoride product of hexafluoropropene oxide polymerization to a perfluoropolyether carboxylic acid. Perfluoropolyether (350 gm, 0.117 mole) having terminal carboxylic acid groups and of average molecular weight 3000 gm/mole and a monel corrosion coupon were heated to 100° C. in an all monel fluorinator, while purging with nitrogen (100 sccm) for 35 minutes. Molecular fluorine diluted with nitrogen was added as follows: 4.8% for 10 minutes, 11.1% for 10 minutes, 20.0% for 10 minutes, 33.3% for 10 minutes and 50.0% for 132 minutes (all with a nitrogen flow rate of 40 sccm). The contents of the reactor were cooled to 120° C. and purged with nitrogen (100 sccm) for 60 minutes. Analysis of the monel corrosion coupon showed corrosion at a rate of 0.00389 cm/month.

I claim:

1. In a process for preparing fluorocarbon polyethers comprising the steps of:
    (a) polymerizing a perfluoroolefin epoxide to form an acid fluoride;
    (b) hydrolyzing the acid fluoride to form a perfluorinated carboxylic acid; and
    (c) neutralizing the acid by heating with fluorine to replace the carboxylic acid end group with a fluorine radical, the improvement comprising heating the acid with fluorine in the presence of a metal fluoride.

2. The process of claim 1 wherein the metal fluoride is selected from sodium fluoride and potassium fluoride.

3. The process of claim 1 or claim 2 wherein the acid is heated to a temperature in the range of 50° to 300° C.

4. The process of claim 3 wherein the acid is heated to a temperature of 100° to 150° C.

5. The process of claim 1 or claim 2 wherein the perfluorinated carboxylic acid has a molecular weight in the range of 500 to 1000.

* * * * *